(12) United States Patent
Essex et al.

(10) Patent No.: US 8,272,387 B2
(45) Date of Patent: Sep. 25, 2012

(54) SYSTEM AND METHOD FOR THE MODIFICATION OF SURGICAL PROCEDURES USING A GRAPHICAL DRAG AND DROP INTERFACE

(75) Inventors: Paul J. Essex, Rancho Santa Margarita, CA (US); Johan Ekvall, Laguna Beach, CA (US); Kirk W. Todd, Yorba Linda, CA (US)

(73) Assignee: Novartis AG, Basel (CH)

( * ) Notice: Subject to any disclaimer, the term of this patent is extended or adjusted under 35 U.S.C. 154(b) by 1378 days.

(21) Appl. No.: 11/479,668

(22) Filed: Jun. 30, 2006

(65) Prior Publication Data

US 2008/0004728 A1    Jan. 3, 2008

(51) Int. Cl.
*A61B 19/00* (2006.01)
*A61B 17/00* (2006.01)

(52) U.S. Cl. ............... 128/898; 606/1; 700/17; 700/83; 700/87

(58) Field of Classification Search ............ 606/1, 4–12, 606/20, 32, 41; 607/88, 89, 96; 600/101, 600/103; 700/11, 17, 83, 87, 90; 128/898
See application file for complete search history.

(56) References Cited

U.S. PATENT DOCUMENTS

| | | | |
|---|---|---|---|
| 4,395,258 A | 7/1983 | Wang et al. | |
| 4,493,695 A | 1/1985 | Cook | |
| 4,627,833 A | 12/1986 | Cook | |
| 4,713,051 A | 12/1987 | Steppe | |
| 4,758,238 A | 7/1988 | Sundblom | |
| 4,790,816 A | 12/1988 | Sundblom | |
| 4,798,850 A | 1/1989 | Brown | |
| 5,455,766 A | 10/1995 | Scheller et al. | |
| 5,554,894 A * | 9/1996 | Sepielli | 307/119 |
| 5,997,528 A | 12/1999 | Bisch et al. | |
| 6,036,458 A | 3/2000 | Cole | |
| 6,059,544 A | 5/2000 | Jung | |
| 6,251,113 B1 | 6/2001 | Appelbaum et al. | |
| 6,267,956 B1 | 7/2001 | Gomes | |
| 6,292,178 B1 | 9/2001 | Bernstein | |
| 6,293,926 B1 | 9/2001 | Sorensen | |
| 6,364,342 B1 | 4/2002 | Kim | |
| 6,602,227 B1 | 8/2003 | Cimino et al. | |
| 6,707,476 B1 | 3/2004 | Hochstedler | |

(Continued)

FOREIGN PATENT DOCUMENTS

EP    1872736 A2    1/2008

(Continued)

OTHER PUBLICATIONS

International Searching Authority, Written Opinion of the International Searching Authority, International Application No. PCT/US2008/067671, Apr. 6, 2009, 5 pages.

(Continued)

*Primary Examiner* — Ahmed Farah (57) ABSTRACT

Embodiments of the present invention provide a system and method for allowing a user to modify a surgical procedure. An embodiment of the method of the present invention can include: providing a GUI on a touch screen of a surgical console, said GUI comprising a representation of the surgical procedure and representations of one or more surgical steps, wherein the GUI allows a user to modify the representation of the surgical procedure by dragging and dropping representations of surgical steps using the touch screen; detecting that the representation of the surgical procedure has been modified; and modifying the surgical procedure to correspond to the modified representation of the surgical procedure.

19 Claims, 7 Drawing Sheets

U.S. PATENT DOCUMENTS

| | | |
|---|---|---|
| 2001/0016711 A1 | 8/2001 | Sorensen |
| 2002/0045887 A1 | 4/2002 | DeHoogh et al. |
| 2002/0193676 A1 | 12/2002 | Bodicker et al. |
| 2003/0202894 A1 | 10/2003 | Leukanech |
| 2003/0204172 A1 | 10/2003 | Steppe |
| 2003/0225363 A1 | 12/2003 | Gordon |
| 2004/0002873 A1 | 1/2004 | Sachfrva |
| 2004/0024384 A1 | 2/2004 | Novak |
| 2004/0074281 A1 | 4/2004 | Lobdell et al. |
| 2004/0106915 A1 | 6/2004 | Thoe |
| 2004/0253129 A1 | 12/2004 | Sorensen |
| 2005/0065462 A1 | 3/2005 | Nazarifar |
| 2005/0113812 A1* | 5/2005 | Viswanathan et al. ............ 606/1 |
| 2005/0186098 A1 | 8/2005 | Davis |
| 2005/0234395 A1 | 10/2005 | Mackool |
| 2005/0234441 A1 | 10/2005 | Bisch |
| 2005/0285025 A1 | 12/2005 | Boukhny et al. |
| 2005/0289173 A1* | 12/2005 | Vacca ........................... 707/102 |
| 2006/0020915 A1 | 1/2006 | Lloyd et al. |
| 2006/0114175 A1 | 6/2006 | Boukhny |
| 2006/0235307 A1 | 10/2006 | Boukhny et al. |
| 2006/0236242 A1 | 10/2006 | Boukhny et al. |
| 2006/0248477 A1 | 11/2006 | Boukhny et al. |
| 2007/0202479 A1 | 8/2007 | Todd et al. |
| 2008/0003555 A1 | 1/2008 | Ekvall et al. |
| 2008/0065243 A1* | 3/2008 | Fallman et al. ................. 700/83 |
| 2009/0048587 A1 | 2/2009 | Avanzino et al. |
| 2009/0049397 A1 | 2/2009 | Boukhny |
| 2009/0118714 A1 | 5/2009 | Teodorescu |
| 2009/0171328 A1 | 7/2009 | Horvath |
| 2009/0182266 A1 | 7/2009 | Gordon et al. |

FOREIGN PATENT DOCUMENTS

| | | |
|---|---|---|
| EP | 1872736 A3 | 4/2008 |
| RU | 2182468 C2 | 12/2000 |
| RU | 2210972 C1 | 8/2003 |
| WO | WO 97/49340 A1 | 12/1997 |
| WO | WO 02/32354 A1 | 4/2002 |
| WO | WO 2005/084570 A1 | 9/2005 |
| WO | WO 2006/060423 A1 | 6/2006 |
| WO | WO 2007/101154 A1 | 9/2007 |
| WO | WO 2009/023376 A2 | 2/2009 |
| WO | WO 2009/023376 A3 | 2/2009 |

OTHER PUBLICATIONS

International Searching Authority, Written Opinion of the International Searching Authority, International Application No. PCT/US2007/062810, Jul. 30, 2007, 6 pages.

http://www.nidek.ru/cv24000.shtml, downloaded Jun. 3, 2011, computer translation by http://translate.google.com/#, 7 pages.

http://goszakaz.perm.ru/, downloaded Aug. 1, 2011, computer translation by http://translate.google.com/#, 6 pages.

Gui, "Nidek CV-24000 A New Page in the History of Ophthalmological Surgery" in the journal "Eye", 2001, No. 3, pp. 27-28 D3.

* cited by examiner

SYSTEM AND METHOD FOR THE MODIFICATION OF SURGICAL PROCEDURES USING A GRAPHICAL DRAG AND DROP INTERFACE

TECHNICAL FIELD OF THE INVENTION

The present invention relates surgical systems and to surgical procedures performed. More particularly, embodiments of the present invention relate to surgical procedure steps used in ophthalmic surgical systems. Even more particularly, embodiments of the present invention relate to systems and methods for modifying, adding or eliminating surgical steps in a surgical procedure.

BACKGROUND

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. Such surgical instrumentation can comprise a Vitreoretinal and Cataract microsurgical console. Such a surgical console can provide a variety of functions depending on the surgical procedure and surgical instrumentation. For example, surgical consoles can expedite cataract surgeries (e.g. phacoemulsification procedures) by helping manage irrigation and aspiration flows into and out of a surgical site. And of course surgical consoles can provide other functions.

Vitreoretinal and Cataract microsurgical consoles can make use of a predefined memorized surgical procedure to facilitate a smooth surgical session. However, during surgery, an unexpected complication can arise (such as unexpected bleeding, partial retinal detachment, posterior capsule rupture, etc.). With existing surgical systems, it is difficult to modify a procedure "on the fly" to address such contingencies. Therefore there is a need for a system and method which allows a user to quickly and reliably modify a surgical procedure to handle unexpected complications.

SUMMARY OF THE INVENTION

Embodiments of the present invention provide a system and method for modifying surgical procedures and creating new surgical procedures which is substantially more convenient, more intuitive, nimbler and swifter than prior art systems and methods of procedure modification and creation using a surgical console. One embodiment of the present invention includes a method for the modification of a surgical procedure. The method can comprise the steps of: providing a GUI on a touch screen of a surgical console, said GUI comprising a representation of the surgical procedure and representations of one or more surgical steps, wherein the GUI allows a user to modify the representation of the surgical procedure by dragging and dropping representations of surgical steps using the touch screen; detecting that the representation of the surgical procedure has been modified; and modifying the surgical procedure to correspond to the modified representation of the surgical procedure. If the representation of the surgical procedure is initially blank, the modified representation of the surgical procedure can represent an entirely new procedure. Additionally, modifications of existing procedures can be saved as new procedures.

Another embodiment of the current invention can include a computer program product comprising a set of computer instructions stored on a computer readable medium, said set of computer instructions comprising instructions executable by a processor to: provide a GUI on a touch screen of a surgical console, said GUI comprising a representation of the surgical procedure and representations of one or more surgical steps, wherein the GUI allows a user to modify the representation of the surgical procedure by dragging and dropping representations of surgical steps using the touch screen; detect that the representation of the surgical procedure has been modified; and modify the surgical procedure implemented by the surgical console to correspond to the modified representation of the surgical procedure. In this manner, existing procedures can be modified and new procedures created.

Yet another embodiment of the invention includes a surgical system comprising a touch screen display, a surgical console and a controller coupled to the touch screen display and the surgical console. The controller can be configured to: provide a GUI on the touch screen display, said GUI comprising a representation of the surgical procedure and representations of one or more surgical steps, wherein the GUI allows a user to modify the representation of the surgical procedure by dragging and dropping representations of surgical steps using the touch screen; detect that the representation of the surgical procedure has been modified; and modify the surgical procedure implemented by the surgical console to correspond to the modified representation of the surgical procedure.

Embodiments of the present invention provide the advantage that the user can conveniently and nimbly modify a surgical procedure. Additionally, new surgical procedures can be created. Embodiments of the present invention provide additional advantages in that modification of the surgical procedure is swift, flexible and intuitive.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the FIGURES, like numerals being used to refer to like and corresponding parts of the various drawings.

Vitreoretinal and Cataract microsurgical consoles can make use of predefined memorized surgical steps to facilitate a smooth surgical session. This allows the surgical console to display only the surgical steps required to complete the surgical procedure at hand. This paradigm is called a "procedural" paradigm. During a procedural paradigm based surgery, an unexpected complication can arise (such as unexpected bleeding, partial retinal detachment, posterior capsule rupture, etc.) which requires modifying the procedural flow of the procedural paradigm. Thus, a surgical console which implements a procedural paradigm requires a way for a user to quickly modify the procedural flow of the procedural paradigm to handle unexpected complications by modifying, eliminating or adding surgical steps.

Embodiments of the present invention solve this problem by using a touch screen to present an interactive graphical user interface ("GUI") to the user. In a preferred embodiment, the user can use the interactive GUI to nimbly modify the procedural flow of the procedure to handle unexpected complications by adding or removing surgical steps to the procedural paradigm through "dragging" and "dropping" surgical steps. Such a method of manipulation is commonly referred to as "drag and drop" and will be familiar to those having ordinary skill in the art. In one embodiment of the invention, dragging and dropping can be accomplished using the input capabilities of the touch screen.

Figure 1:
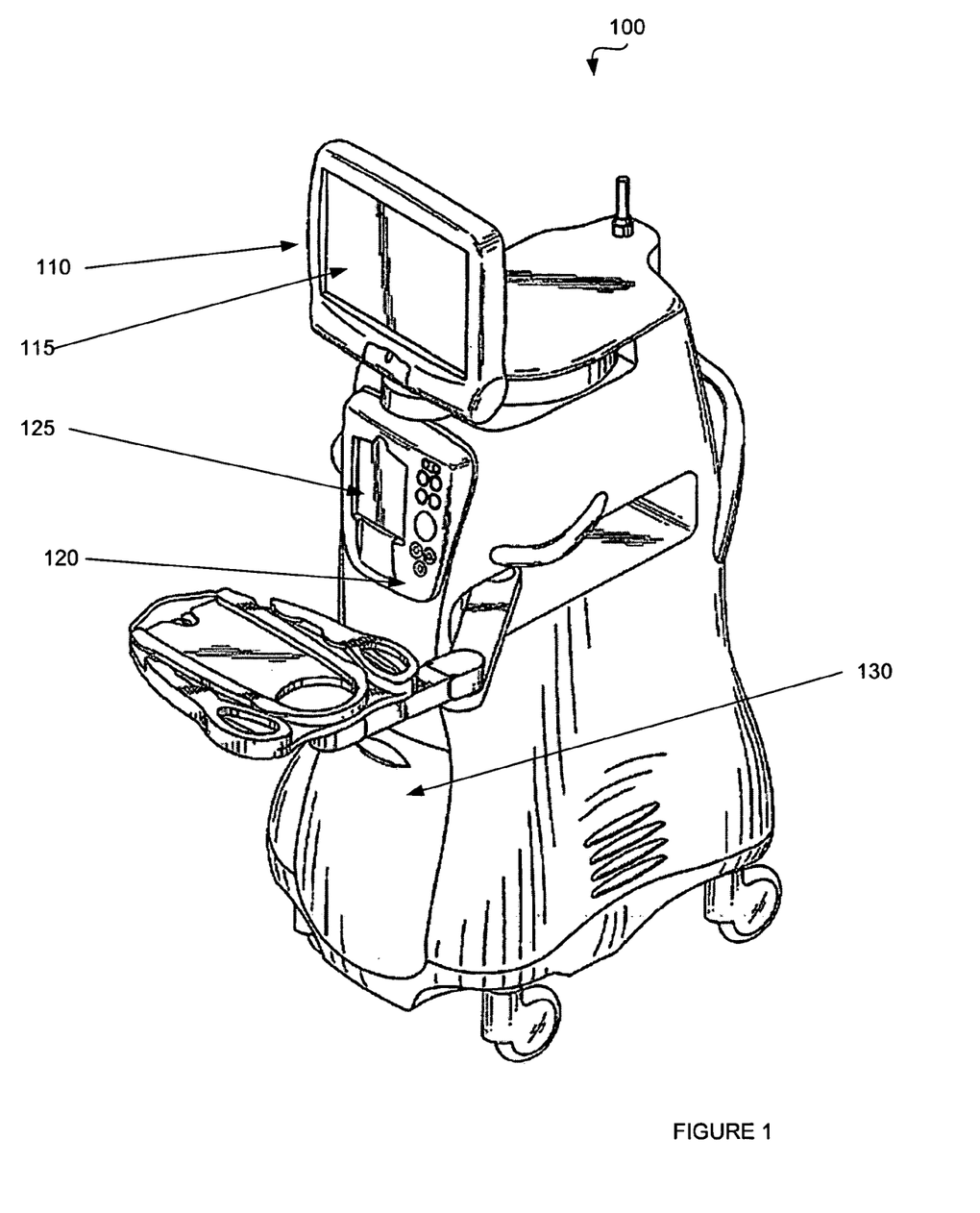
FIG. 1 is a diagrammatic representation of one embodiment of a surgical console.

FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a GUI that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features.

In operation, the GUI can be used to display surgical steps comprising a procedural paradigm. The GUI can further display additional surgical steps which can be added to the procedure. These additional surgical steps can be added to the procedure by a simple "drag and drop." Surgical steps can also be removed from the procedure by a "drag and drop." Thus, the procedural flow of the procedural paradigm can be nimbly manipulated by a user to handle complications.

Surgical console 100 is provided by way of example and embodiments of the present invention can be implemented with a variety of surgical systems. Example surgical systems in which various embodiments of the present invention can be used include, for example, the Series 2000® Legacy® cataract surgical system, the Accurus® 400VS surgical system, the Infiniti™ Vision System surgical system all available from Alcon Laboratories Inc. of Fort Worth, Tex. Embodiments of the present invention can be implemented in other suitable surgical systems having a touch screen as would be understood by one of ordinary skill in the art.

Figure 2:
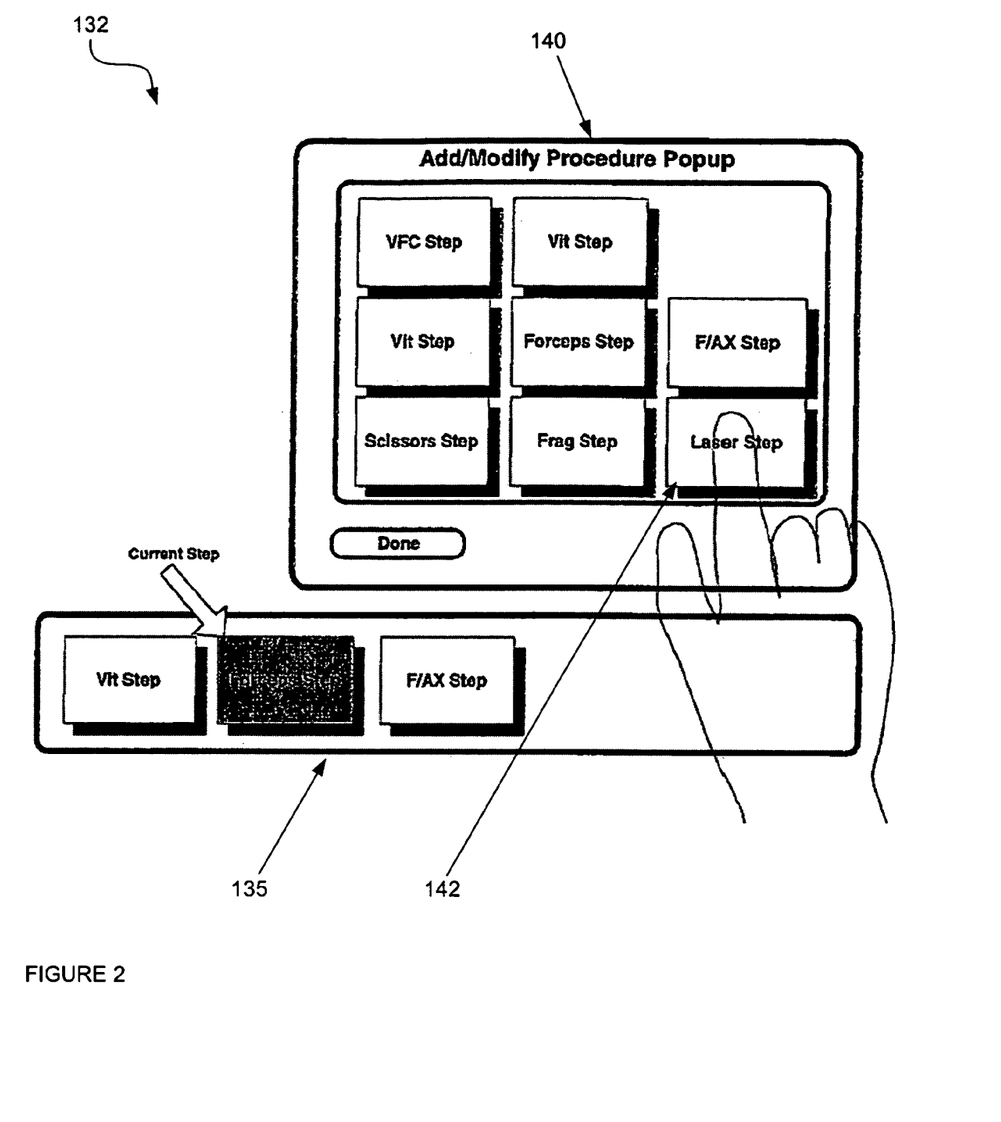
FIG. 2 is a representation of one embodiment of a graphical user interface (GUI)

FIG. 2 shows an embodiment of a GUI 132 which might be displayed on a surgical console touch screen (e.g. touch screen 115 of FIG. 1). As shown in FIG. 2, GUI 132 comprises a portion that displays a representation of a surgical procedure. For example, GUI 132 can comprise a procedural paradigm display 135 which displays the procedural paradigm. As shown in FIG. 2, GUI 132 further comprises a surgical step display 140 that displays representations of various surgical steps. The displayed surgical steps can be added to the procedure at the appropriate stage in the procedural flow to modify the procedure to handle complications as they arise. In FIG. 2, a user has selected the Laser Step by pressing the representation of the Laser Step 142 shown on the touch screen.

Procedural paradigm display 135 and surgical steps display 140 can be manifested in any number of ways and combinations, including appearing together on the same touch screen or on different screens or any conceivable combination thereof. Furthermore, procedural paradigm display 135 and surgical steps display 140 can be combined to comprise one display.

Figure 3:
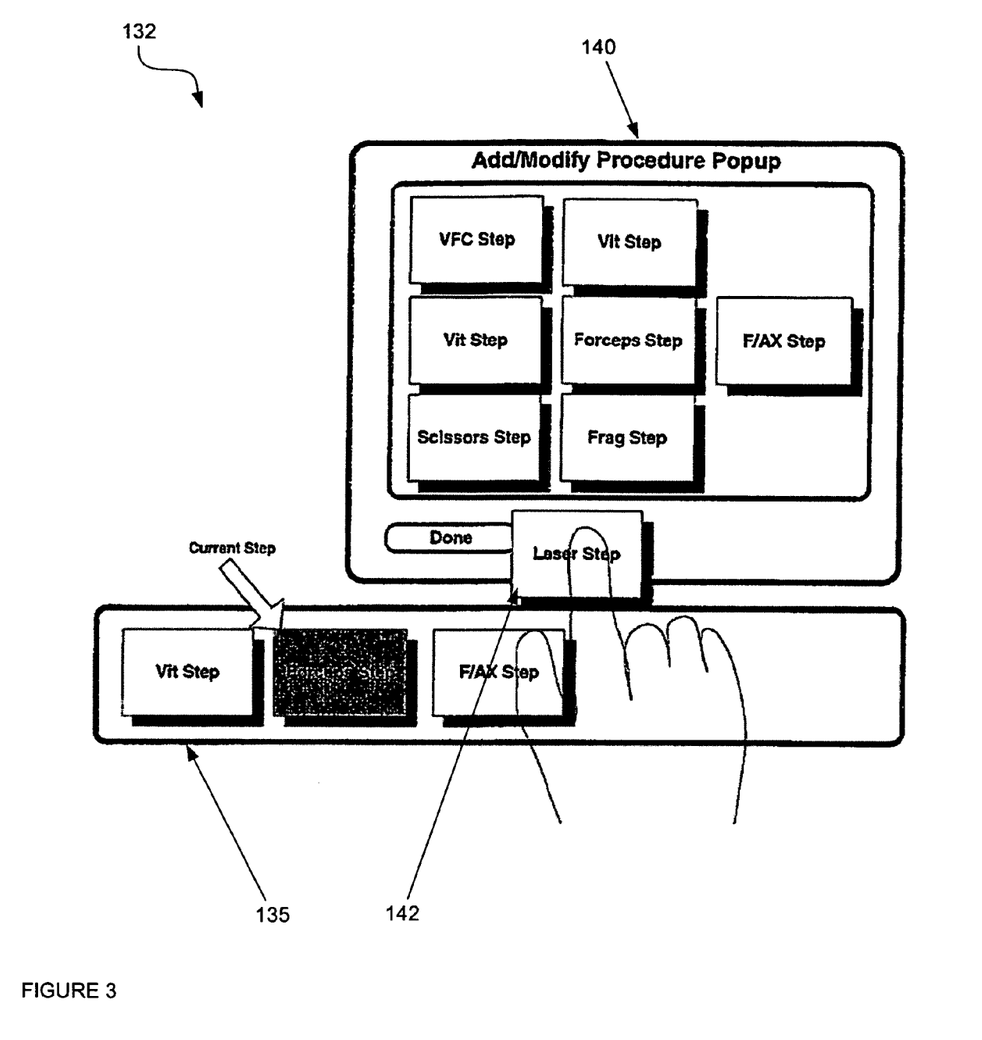
FIG. 3 is a representation of one embodiment of a GUI.

FIG. 3 shows an embodiment of GUI 132 during the "drag" portion of modifying a procedure. The displayed surgical steps can be added to the procedure at the appropriate stage in the procedural flow to modify the procedure to handle complications as they arise. In FIG. 3, the user has begun to move representation of the Laser Step 142 from surgical steps display 140 to procedural paradigm display 135 by "dragging" representation of the Laser Step 142 across the touch screen.

Figure 4:
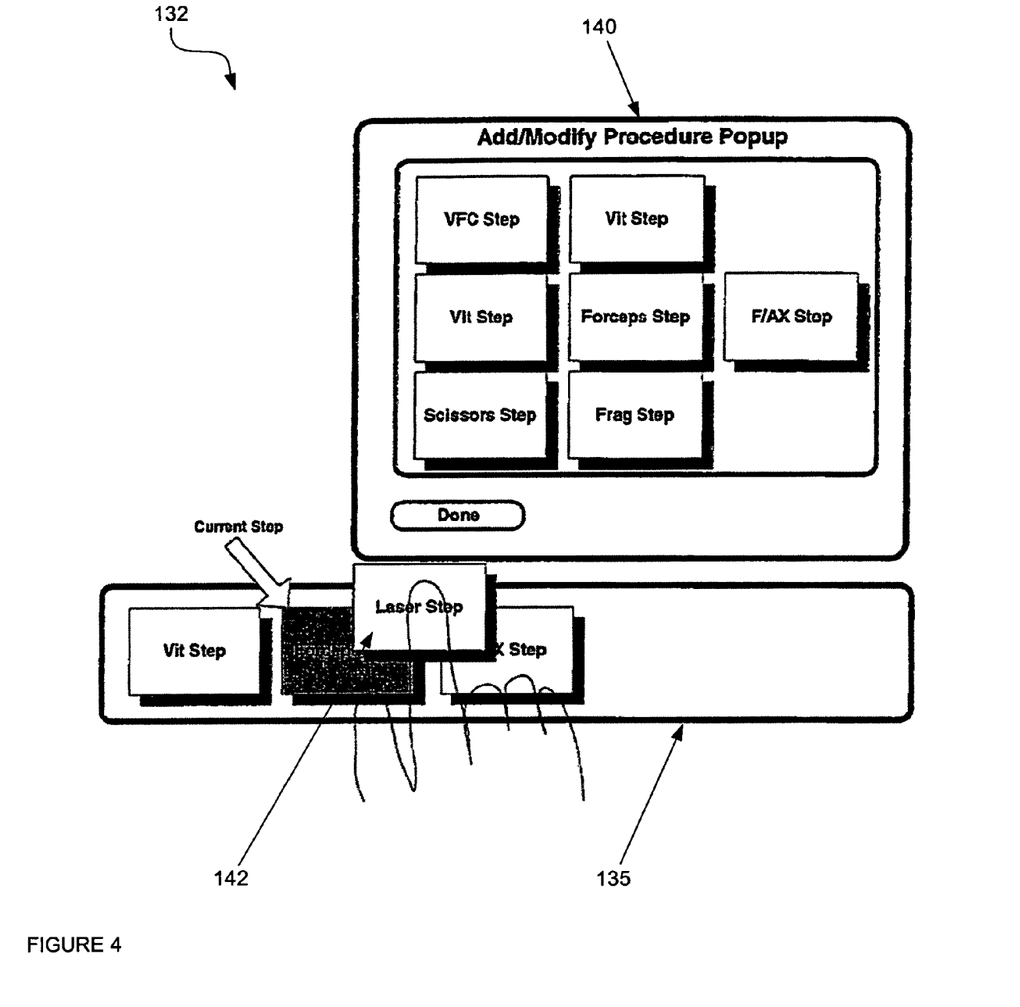
FIG. 4 is a representation of one embodiment of a GUI.

FIG. 4 shows an embodiment of GUI 132 as the user selects the location for the Laser Step. The displayed surgical steps can be added to the procedure at the appropriate stage in the procedural flow to modify the procedure to handle complications as they arise. In FIG. 4, the user has moved representation of the Laser Step 142 from surgical steps display 140 to procedural paradigm display 135 by "dragging" representation of the Laser Step 142 across the touch screen.

Figure 5:
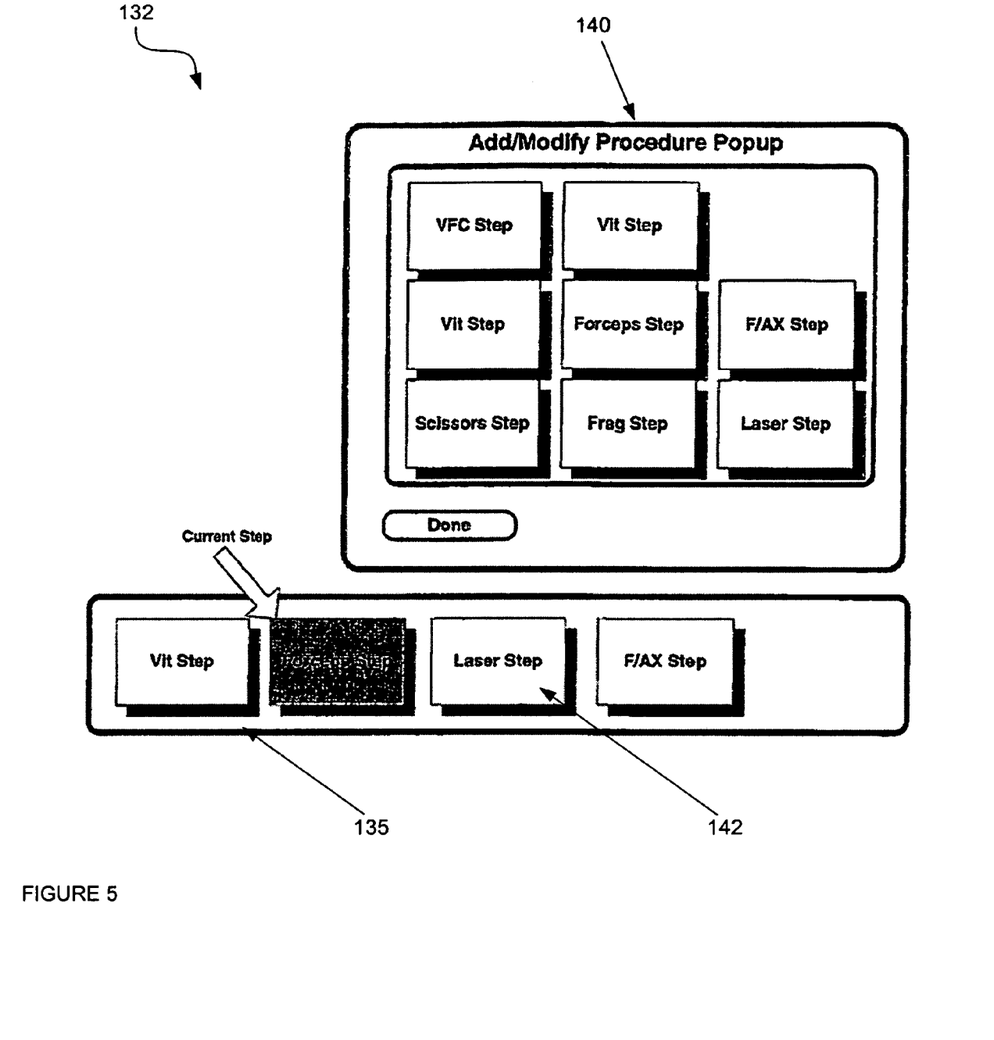
FIG. 5 is a representation of one embodiment of a GUI.

FIG. 5 shows an embodiment of GUI 132 after the "drop." In FIG. 5, the user has added the Laser Step to the procedural paradigm by "dropping" representation of the Laser Step 142 at the appropriate stage in procedural paradigm display 135. Consequently, the underlying procedure can be modified to add the Laser Step to the steps of the procedure initially displayed in procedural paradigm display 135.

While the foregoing embodiment of the invention described above and represented in FIGS. 2 through 5 continuously displays both the surgical steps display and the procedural paradigm display, this is by way of example and embodiments of the present invention can be implemented in other ways. For example, the surgical steps display need not be continuously displayed, but can be dismissed by a user or automatically disappear once a surgical step has been selected. Furthermore, the surgical step display may be initially absent from the GUI and may be summoned by the user when desired (e.g. by touching an add/modify button in the GUI or by any other suitable mechanism). Similarly, in another embodiment, the procedural paradigm display may initially be absent and summoned by the user when desired. Furthermore, in another embodiment, the user may dismiss the procedural paradigm display when user wishes.

The user can also modify the procedure by removing surgical step(s) using the same drag and drop methodology. For example, a user can select a surgical step in the procedure which is to be removed from the procedural paradigm by touching the representation of said surgical step displayed in the procedural paradigm display on the touch screen. The user can then "drag" the selected representation of the surgical step to be removed out of the procedural paradigm display. The user "drops" the selected representation of the surgical step to be removed by removing user's finger from the touch screen. This process effects the removal of the selected surgical step from the procedural paradigm. Similarly, the user can modify the order of steps in a procedure by rearranging the representations of the steps in the GUI by dragging and dropping the representations.

Figure 6:
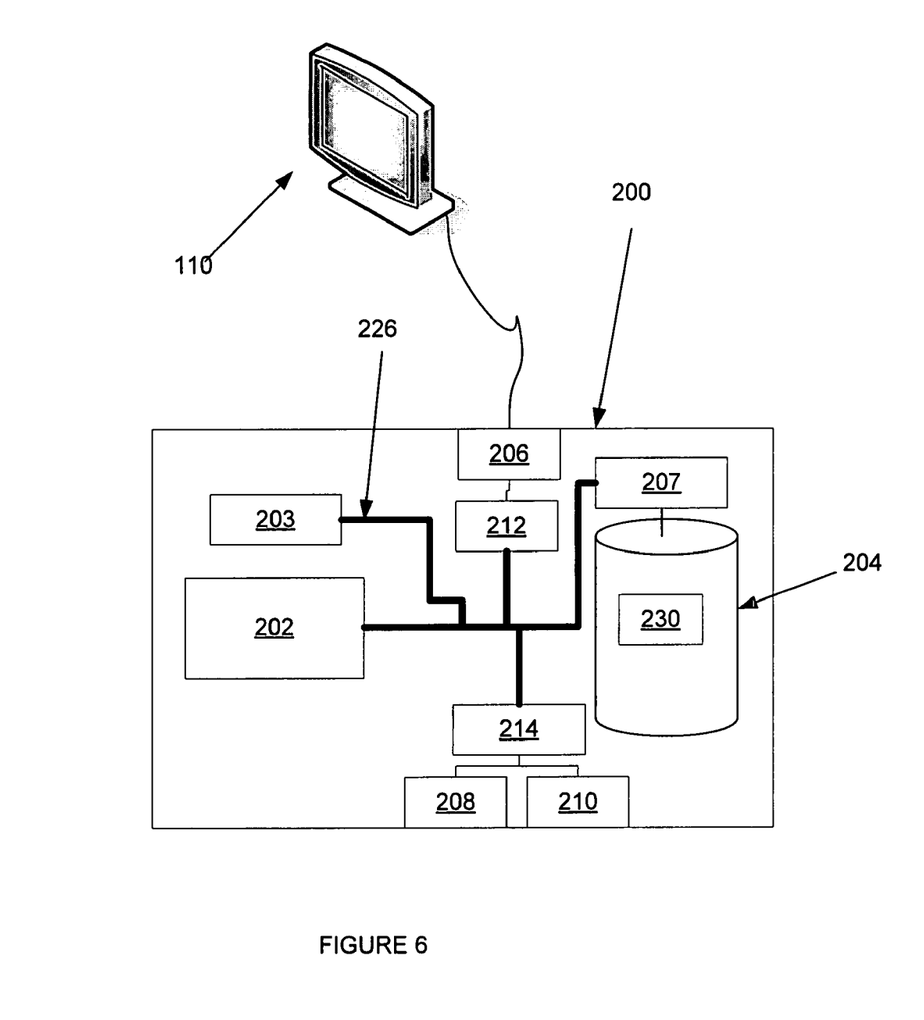
FIG. 6 is a diagrammatic representation of one embodiment of a controller for surgical instrumentation.

FIG. 6 is a diagrammatic representation of a surgical instrumentation controller 200 ("controller 200"). Controller 200 can be onboard or connected to surgical instrumentation such as surgical console 100. Controller can include a processor 202, such as an Intel Pentium 4 based processor (Intel and Pentium are trademarks of Intel Corporation of Santa Clara, Calif.), a primary memory 203 (e.g., RAM, ROM, Flash Memory, EEPROM or other computer readable medium known in the art) and a secondary memory 204 (e.g., a hard drive, disk drive, optical drive or other computer readable medium known in the art). A memory controller 207 can control access to secondary memory 204. Controller 200 can include I/O interfaces, such as touch screen interface 206. A video controller 212 can control interactions over the touch screen interface 206. Similarly, an I/O controller 214 can control interactions over I/O interfaces 208 and 210. Controller 200 can include a variety of input devices. Various components of controller 200 can be connected by a bus 226.

Secondary memory 204 can store a variety of computer instructions that include, for example, an operating system such as a Windows operating system (Windows is a trademark of Redmond, Wash. based Microsoft Corporation) and applications that run on the operating system, along with a variety of data. More particularly, secondary memory 204 can store a software program 230 that controls the procedural flow of a surgery based on a procedural paradigm. During execution by processor 202, portions of program 230 can be stored in secondary memory 204 and/or primary memory 203.

In operation, program 230 can be executable by processor 202 to provide a GUI to the user (e.g., through monitor 110) that shows a first display which represents the procedural paradigm and which further shows a second display which represents surgical steps that can be added to the procedural paradigm. This second display is comprised of representations of surgical steps. The user can select a surgical step to add to the procedural paradigm by touching the representation of the desired surgical step in the second display. The user can then "drag" the selected surgical step to the desired stage in the procedural shown in the first display using the input capabilities of the touch screen. The user can then "drop" the selected surgical step at the desired stage by removing his finger from the touch screen. The representation of the desired surgical step will be shown at the desired stage in the procedural shown in the first display.

When controller 200 receives notice of a modification of the procedure (e.g., by detecting input from the touch screen) controller 200 will modify the procedural flow of the surgical procedure as implemented by the surgical consol to correspond to the procedure as shown on the touch screen.

Controller 200 of FIG. 6 is provided by way of example only and it should be understood that embodiments of the present invention can implemented as a set of computer instructions stored on a computer readable medium in a variety of computing devices. Program 230 can be executable to receive and store data over a network and can include instructions that are stored at a number of different locations and are executed in a distributed manner. While shown as a stand alone program in FIG. 6, it should be noted that program 230 can be a module of a larger program, can comprise separate programs operable to communicate data to each other or can be implemented according to any suitable programming architecture and language.

Figure 7:
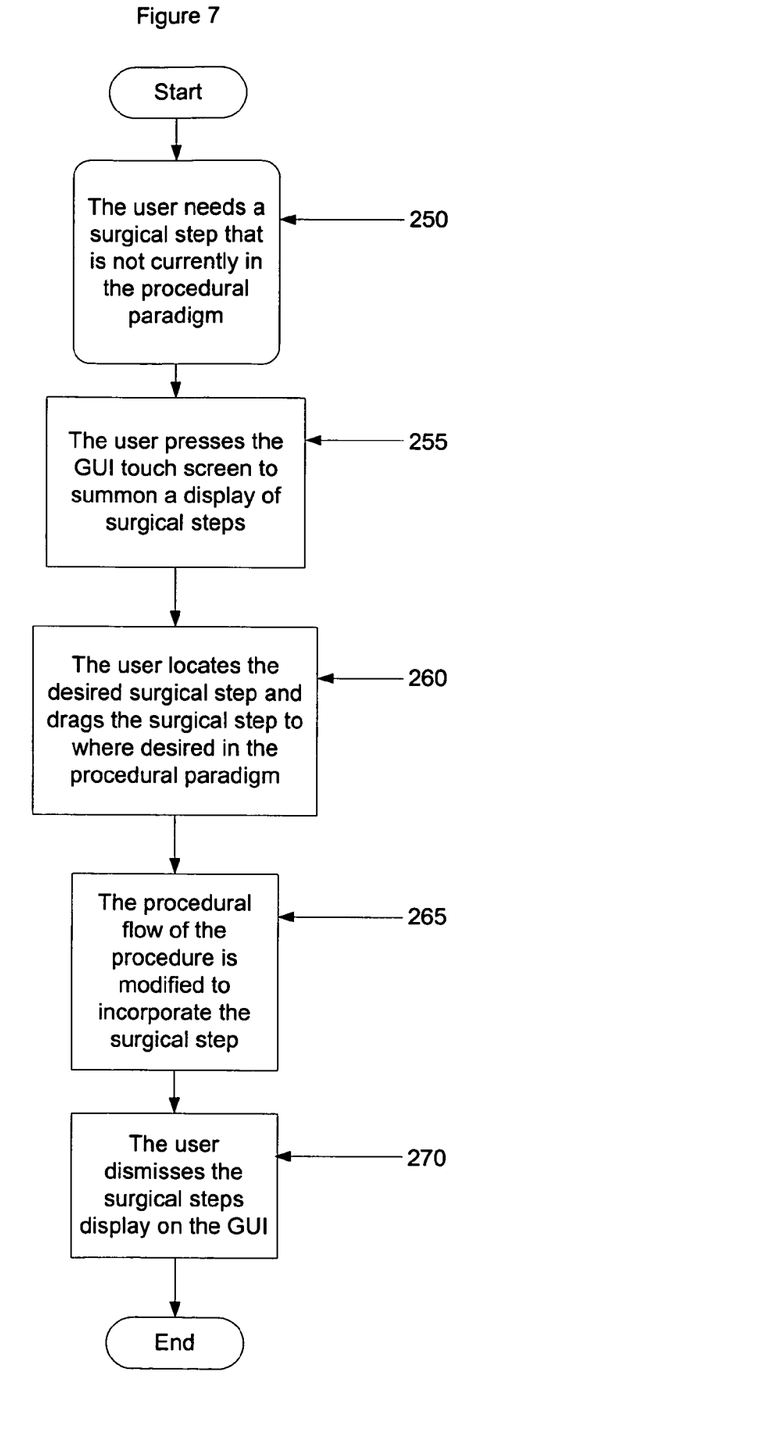
FIG. 7 is a flow chart illustrating one embodiment of a method for modifying a surgical procedure using the input capabilities of a touch screen.

FIG. 7 is a flow chart illustrating one embodiment of a method for modifying the procedural flow of a procedure. The method of FIG. 7 can be implemented as a set of computer executable instructions stored on a computer readable medium at, for example, surgical console 100. The set of computer executable instructions can, when executed, present the user with an interactive user interface (e.g., a GUI) on a touch screen 115 that allows the user to modify a procedure by adding or removing surgical steps through dragging and dropping representations of surgical steps displayed on the interactive user interface. At step 250, the user develops a need for a surgical step not currently in the procedure.

At step 255, the user uses the GUI displayed on touch screen 115 to summon a surgical steps display which displays representations of surgical steps. At step 260, the user drags the representation of the desired surgical step to where desired in the representation of the procedure shown on the GUI and drops the representation of the surgical step at the desired location in the representation of the procedure. The procedural flow of the procedure is then modified to incorporate the surgical step into the procedure at the desired stage (step 265). At step 270, the user dismisses the surgical steps display shown on the GUI. In an implementation that utilizes a procedural paradigm, the new procedural flow can be optionally saved as a new paradigm.

The steps of FIG. 7 can be repeated as needed or desired. Moreover,

FIG. 7 is provided by way of example and embodiments of the present invention can implement the steps in different orders or provide greater functionality. Additionally, such "drag and drop" functionality can be used to remove steps from a procedure or change the order of steps in the procedure.

Embodiments of the present invention can be used in a variety of surgical systems, particularly vision systems, and provide increased functionality and ease of use. Users are able to swiftly modify a surgical procedure to cope with arising complications. For example, users will be able to nimbly add or remove surgical steps from a surgical procedure simply by dragging and dropping on a touch screen.

Although the present invention has been described in detail herein with reference to the illustrated embodiments, it should be understood that the description is by way of example only and is not to be construed in a limiting sense. It is to be further understood, therefore, that numerous changes in the details of the embodiment of this invention and additional embodiments of this invention will be apparent, and may be made by, persons of ordinary skill in the art having reference to this description. It is contemplated that all such changes and additional embodiments are within scope of the invention as claimed below.

The invention claimed is:

1. A method for modification of a surgical procedure, comprising:
   providing a Graphical User Interface (GUI) on a touch screen of a surgical console, said GUI comprising a representation of the surgical procedure and representations of one or more surgical steps;
   receiving an indication that the representation of the surgical procedure has been modified by a user through dragging and dropping representations of surgical steps using the GUI on the touch screen;
   detecting that the representation of the surgical procedure has been modified by addition or removal of a representation of a surgical step to/from the representation of the surgical procedure; and modifying the surgical procedure to correspond to the modified representation of the surgical procedure.

2. The method of claim 1, wherein the representation of the surgical procedure comprises representations of surgical steps to be performed.

3. The method of claim 2, wherein the GUI further comprises an area including representations of surgical steps.

4. The method of claim 3, wherein a surgical step is added to the surgical procedure based on dragging a corresponding representation of the surgical step from the area including representations of surgical steps and dropping the corresponding representation of the surgical step at the desired stage in the representation of the surgical procedure.

5. The method of claim 1, wherein a surgical step is removed from the surgical procedure based on dragging a corresponding representation of the surgical step from the representation of the procedure and dropping the corresponding representation of the surgical step outside of the representation of the surgical procedure.

6. The method of claim 1, further comprising:
receiving an indication that the representation of the surgical procedure has been modified by a user through dragging and dropping representations of surgical steps within the representation of the surgical procedure using the GUI on the touch screen; and
detecting that the representation of the surgical procedure has been modified by movement of a representation of a surgical step within the representation of the surgical procedure; and
re-ordering the surgical procedure to correspond to the modified representation of the surgical procedure.

7. The method of claim 1, further comprising:
during actual performance of the surgical procedure, displaying only the representations of the surgical steps in the surgical procedure as modified by the user.

8. A surgical system comprising:
a touch screen display;
a surgical console; and
a controller coupled to the touch screen display and the surgical console, the controller configured to:
provide a Graphical User Interface (GUI) on the touch screen display, said GUI comprising a representation of a surgical procedure and representations of one or more surgical steps;
receive an indication that the representation of the surgical procedure has been modified by a user through dragging and dropping representations of surgical steps using the GUI on the touch screen;
detect that the representation of the surgical procedure has been modified by addition or removal of a surgical step to/from the representation of the surgical procedure; and
modify the surgical procedure implemented by the surgical console to correspond to the modified representation of the surgical procedure.

9. The surgical system of claim 8, wherein the representation of the surgical procedure comprises representations of surgical steps to be performed.

10. The surgical system of claim 9, wherein the GUI further comprises an area including representations of surgical steps.

11. The surgical system of claim 10, wherein a surgical step is added to the surgical procedure based on dragging a corresponding representation of the surgical step from the area including representations of surgical steps and dropping the corresponding representation of the surgical step at the desired stage in the representation of the surgical procedure.

12. The surgical system of claim 8, wherein a surgical step is removed from the surgical procedure based on dragging a corresponding representation of the surgical step from the representation of the procedure and dropping the corresponding representation of the surgical step outside of the representation of the surgical procedure.

13. The surgical system of claim 8, wherein the controller is further configured to:
receive an indication that the representation of the surgical procedure has been modified by a user through dragging and dropping representations of surgical steps within the representation of the surgical procedure using the GUI on the touch screen; and
detect that the representation of the surgical procedure has been modified by movement of a representation of a surgical step within the representation of the surgical procedure; and
re-order the surgical procedure to correspond to the modified representation of the surgical procedure.

14. The surgical system of claim 8, wherein the controller is further configured to:
during actual performance of the surgical procedure, display only the representations of the surgical steps in the surgical procedure as modified by the user.

15. A computer program product comprising a set of computer instructions stored on a computer readable medium, said set of computer instructions comprising instructions executable by a processor to:
provide a Graphical User Interface (GUI) on a touch screen of a surgical console, said GUI comprising a representation of a surgical procedure and representations of one or more surgical steps;
receive an indication that the representation of the surgical procedure has been modified by a user through dragging and dropping representations of surgical steps using the GUI on the touch screen;
detect that the representation of the surgical procedure has been modified by addition or removal of a surgical step to/from the representation of the surgical procedure; and
modify the surgical procedure implemented by the surgical console to correspond to the modified representation of the surgical procedure.

16. The computer program product of claim 15, wherein the representation of the surgical procedure comprises representations of surgical steps to be performed.

17. The computer program product of claim 16, wherein the GUI further comprises an area including representations of surgical steps.

18. The computer program product of claim 17, wherein a surgical step is added to the surgical procedure based on dragging a corresponding representation of the surgical step from the area including representations of surgical steps and dropping the corresponding representation of the surgical step at the desired stage in the representation of the surgical procedure.

19. The computer program product of claim 15, wherein a surgical step is removed from the surgical procedure based on dragging a corresponding representation of the surgical step from the representation of the procedure and dropping the corresponding representation of the surgical step outside of the representation of the surgical procedure.

* * * * *